US011067706B2

(12) United States Patent
Furumoto et al.

(10) Patent No.: US 11,067,706 B2
(45) Date of Patent: Jul. 20, 2021

(54) RADIATION IMAGE SENSING APPARATUS, RADIATION IMAGE SENSING SYSTEM, CONTROL METHOD FOR RADIATION IMAGE SENSING APPARATUS, AND NON-TRANSITORY COMPUTER-READABLE STORAGE MEDIUM

(71) Applicant: CANON KABUSHIKI KAISHA, Tokyo (JP)

(72) Inventors: Kazuya Furumoto, Atsugi (JP); Minoru Watanabe, Yokohama (JP); Kentaro Fujiyoshi, Tokyo (JP)

(73) Assignee: CANON KABUSHIKI KAISHA, Tokyo (JP)

( * ) Notice: Subject to any disclaimer, the term of this patent is extended or adjusted under 35 U.S.C. 154(b) by 0 days.

(21) Appl. No.: 16/594,611

(22) Filed: Oct. 7, 2019

(65) Prior Publication Data

US 2020/0041664 A1 Feb. 6, 2020

Related U.S. Application Data

(63) Continuation of application No. PCT/JP2018/005769, filed on Feb. 19, 2018.

(30) Foreign Application Priority Data

Apr. 27, 2017 (JP) .............................. JP2017-088782

(51) Int. Cl.
*G01T 1/208* (2006.01)
*H04N 5/32* (2006.01)
(Continued)

(52) U.S. Cl.
CPC .............. *G01T 1/208* (2013.01); *A61B 6/488* (2013.01); *A61B 6/5205* (2013.01); *A61B 6/542* (2013.01);
(Continued)

(58) Field of Classification Search
CPC ......... G01T 1/208; G01T 1/023; G01T 1/026; G01T 1/1614; A61B 6/488; A61B 6/5205; G01N 23/083; G06T 5/50; H04N 5/374
See application file for complete search history.

(56) References Cited

U.S. PATENT DOCUMENTS 6,617,562 B1 * 9/2003 Mann ................ H01L 27/14609
250/208.1
7,465,933 B2 12/2008 Ishii et al.
(Continued)

FOREIGN PATENT DOCUMENTS

JP  2012-015913  1/2012
JP  2013-180134  9/2013
(Continued)

OTHER PUBLICATIONS

U.S. Appl. No. 16/672,824, Sho Sato, filed Nov. 4, 2019.
(Continued)

*Primary Examiner* — Michael C Bryant
(74) *Attorney, Agent, or Firm* — Venable LLP

(57) ABSTRACT

A radiation image sensing apparatus is provided. The apparatus comprises an image sensing area where conversion elements are arranged and used in an image sensing operation of acquiring a radiation image, a detection element configured to detect a radiation dose of radiation entering the image sensing area, a readout unit and a controller. The controller corrects a detection signal read out from the detection element by the readout unit during incidence of radiation in a second image sensing operation performed next to a first image sensing operation, based on a correction amount acquired based on a correction signal read out from the detection element by the readout unit after an end of the incidence of the radiation in the first image sensing operation, and detects a dose of incident radiation in the second
(Continued)

image sensing operation based on the corrected detection signal.

17 Claims, 10 Drawing Sheets

(51) Int. Cl.
    *G01T 1/02*     (2006.01)
    *A61B 6/00*     (2006.01)
    *G01N 23/083*     (2018.01)
    *G06T 5/50*     (2006.01)

(52) U.S. Cl.
    CPC .......... *G01N 23/083* (2013.01); *G01T 1/023* (2013.01); *G06T 5/50* (2013.01); *H04N 5/32* (2013.01)

(56) References Cited

U.S. PATENT DOCUMENTS

| | | | |
|---|---|---|---|
| 7,535,506 B2 | 5/2009 | Nomura et al. | |
| 7,541,617 B2 | 6/2009 | Mochizuki et al. | |
| 7,629,564 B2 | 12/2009 | Mochizuki et al. | |
| 7,645,976 B2 | 1/2010 | Watanabe et al. | |
| 7,750,422 B2 | 7/2010 | Watanabe et al. | |
| 7,812,313 B2 | 10/2010 | Mochizuki et al. | |
| 7,812,317 B2 | 10/2010 | Watanabe et al. | |
| 7,858,947 B2 | 12/2010 | Mochizuki et al. | |
| 7,923,695 B2 | 4/2011 | Ishii et al. | |
| 7,932,946 B2 | 4/2011 | Ishii et al. | |
| 8,067,743 B2 | 11/2011 | Ishii et al. | |
| 8,084,745 B2 | 12/2011 | Mochizuki et al. | |
| 8,154,641 B2 | 4/2012 | Nomura et al. | |
| 8,368,027 B2 | 2/2013 | Ishii et al. | |
| 8,513,611 B2 | 8/2013 | Okada | |
| 8,519,344 B2 | 8/2013 | Ishii et al. | |
| 8,680,472 B2 | 3/2014 | Mochizuki et al. | |
| 8,878,972 B2 | 11/2014 | Wayama et al. | |
| 9,198,271 B2 | 11/2015 | Miyachi | |
| 9,270,903 B2 | 2/2016 | Wayama et al. | |
| 9,277,896 B2 | 3/2016 | Ofuji et al. | |
| 9,423,513 B2 | 8/2016 | Watanabe et al. | |
| 9,521,347 B2 | 12/2016 | Kawanabe et al. | |
| 9,625,585 B1 | 4/2017 | Yokoyama et al. | |
| 9,661,240 B2 | 5/2017 | Fujiyoshi et al. | |
| 9,675,307 B2 | 6/2017 | Ofuji et al. | |
| 9,726,767 B2 | 8/2017 | Kawanabe et al. | |
| 9,835,732 B2 | 12/2017 | Fujiyoshi et al. | |
| 9,838,638 B2 | 12/2017 | Furumoto et al. | |
| 9,948,871 B2 | 4/2018 | Wayama et al. | |
| 10,068,943 B2 | 9/2018 | Fujiyoshi et al. | |
| 10,473,801 B2 | 11/2019 | Kawanabe et al. | |
| 10,537,295 B2 | 1/2020 | Watanabe et al. | |
| 2013/0230141 A1* | 9/2013 | Miyachi | G01N 23/04 378/62 |
| 2013/0342514 A1 | 12/2013 | Yokoyama et al. | |
| 2014/0151769 A1 | 6/2014 | Wayama et al. | |
| 2014/0154833 A1 | 6/2014 | Wayama et al. | |
| 2017/0090041 A1* | 3/2017 | Yokoyama | G01T 1/023 |
| 2018/0008215 A1 | 1/2018 | Wayama et al. | |
| 2018/0231672 A1 | 8/2018 | Yokoyama et al. | |
| 2019/0146103 A1 | 5/2019 | Ofuji et al. | |
| 2019/0391629 A1 | 12/2019 | Yokoyama et al. | |
| 2020/0008766 A1 | 1/2020 | Watanabe et al. | |

FOREIGN PATENT DOCUMENTS

| | | | |
|---|---|---|---|
| JP | 2016-111432 | | 6/2016 |
| JP | 2016111432 A | * | 6/2016 |
| JP | 2017-067501 | | 4/2017 |

OTHER PUBLICATIONS

U.S. Appl. No. 16/686,589, Kentaro Fujiyoshi, filed Nov. 18, 2019.
U.S. Appl. No. 16/720,989, Katsuro Takenaka, filed Dec. 19, 2019.

* cited by examiner

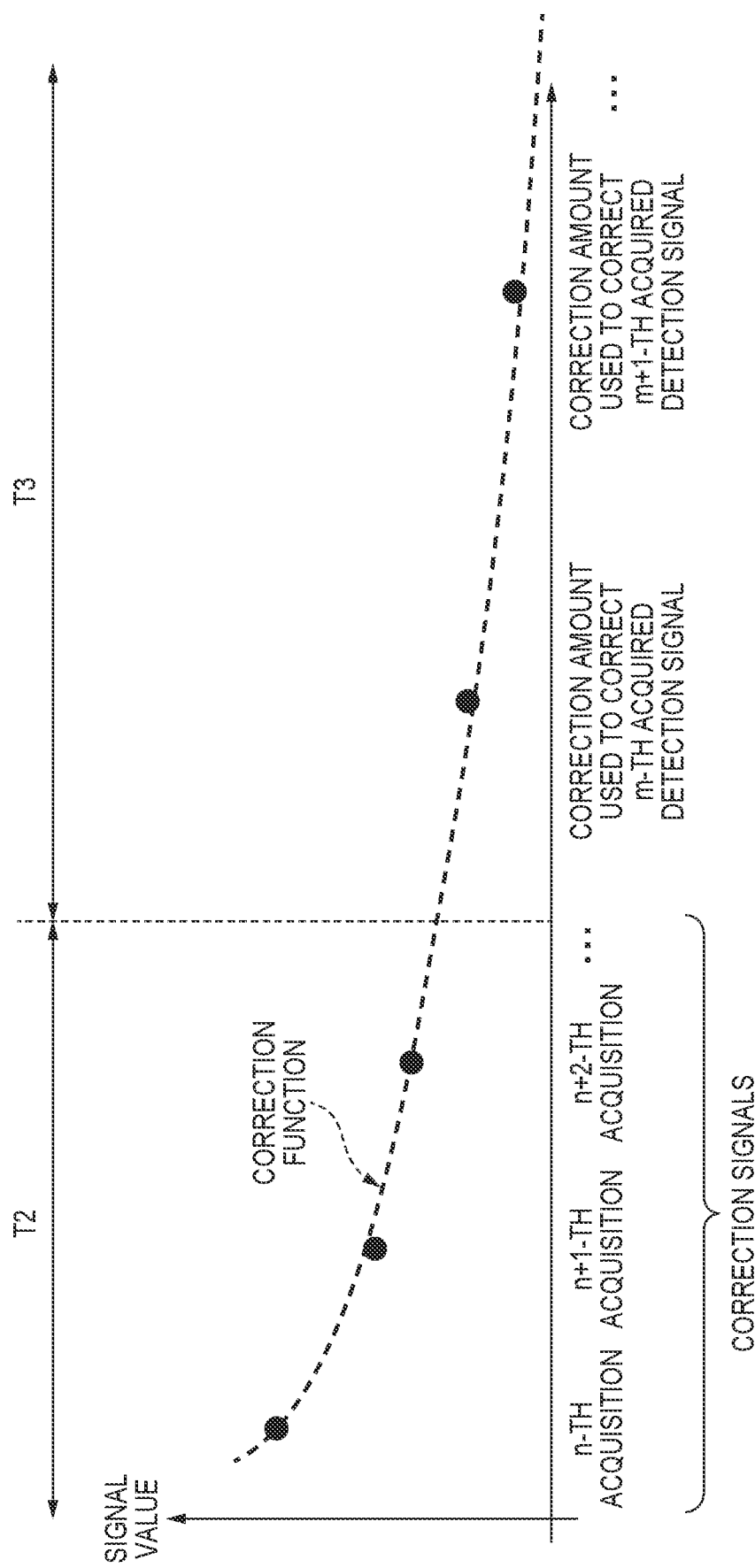

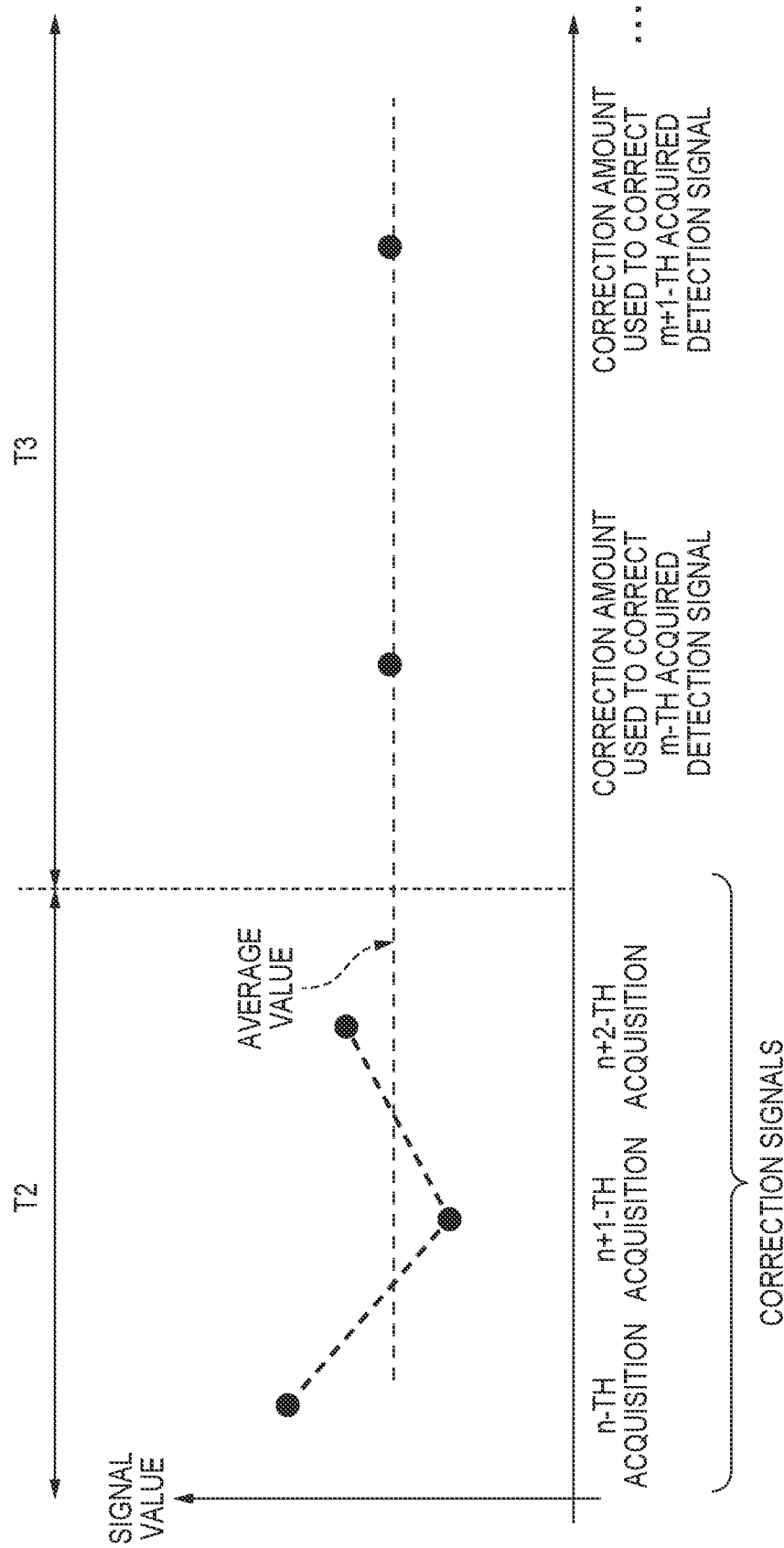

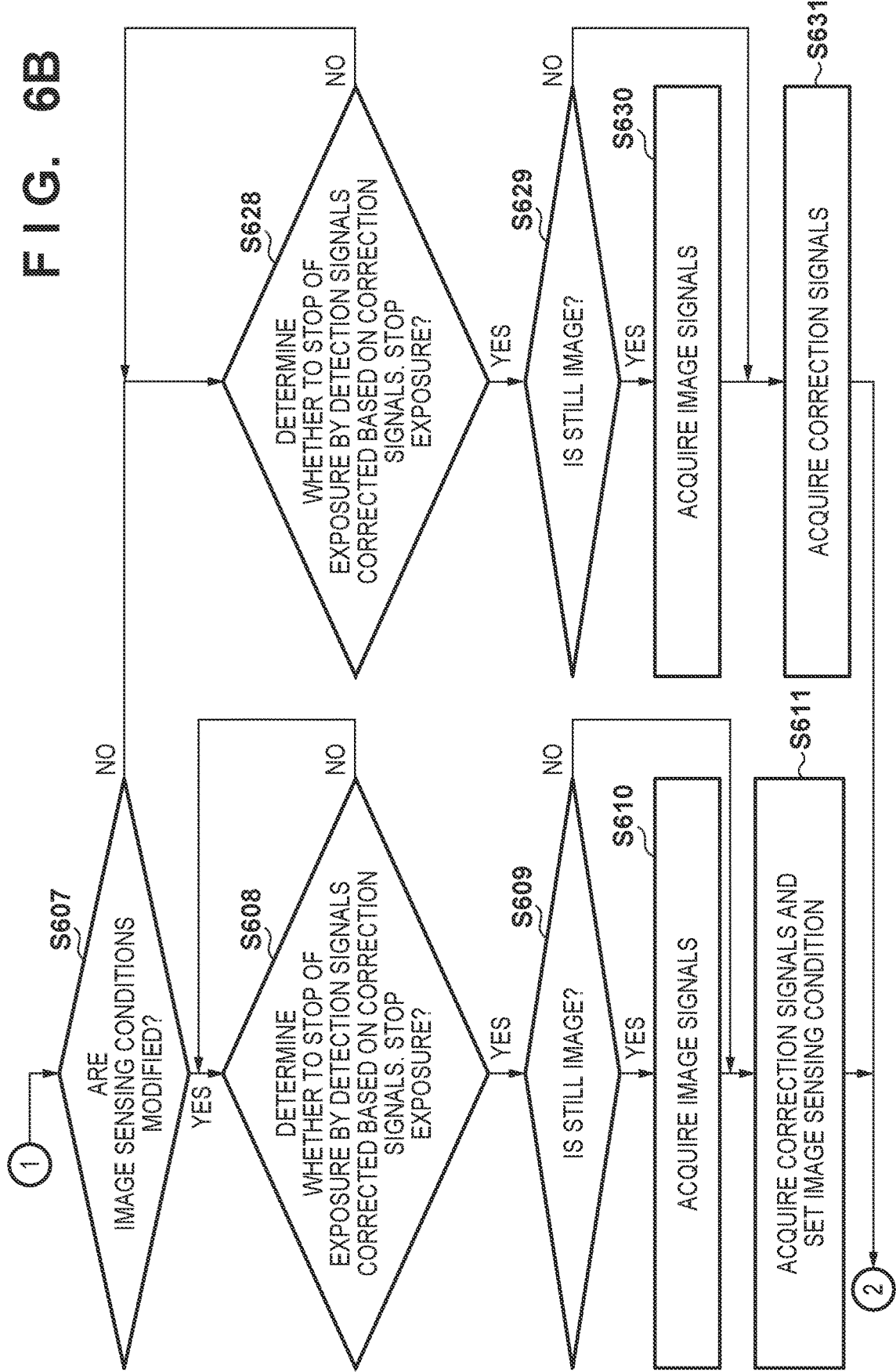

RADIATION IMAGE SENSING APPARATUS, RADIATION IMAGE SENSING SYSTEM, CONTROL METHOD FOR RADIATION IMAGE SENSING APPARATUS, AND NON-TRANSITORY COMPUTER-READABLE STORAGE MEDIUM

CROSS-REFERENCE TO RELATED APPLICATIONS

This application is a Continuation of International Patent Application No. PCT/JP2018/005769, filed Feb. 19, 2018, which claims the benefit of Japanese Patent Application No. 2017-088782, filed Apr. 27, 2017, both of which are hereby incorporated by reference herein in their entirety.

BACKGROUND OF THE INVENTION

Field of the Invention

The present invention relates to a radiation image sensing apparatus, a radiation image sensing system, a control method for the radiation image sensing apparatus, and a non-transitory computer-readable storage medium.

Background Art

A popular image sensing apparatus used in medical image diagnosis or nondestructive inspection is a radiation image sensing apparatus using an image sensing panel on which pixels are arrayed. Each pixel includes a combination of a conversion element that converts radiation into charges, and a switching element such as a thin-film transistor (TFT). The radiation image sensing apparatus is known to detect a radiation dose in real time. Real-time detection of the radiation dose makes it possible to detect the start and end of irradiation with radiation, grasp the integrated dose of incident radiation during the irradiation with radiation, and perform automatic exposure control (AEC). Japanese Patent Laid-Open No. 2012-15913 discloses a method in which a plurality of pixels arranged in a detection area for detecting radiation are set in advance as pixels for acquiring a radiation image and pixels for detecting radiation, and the start of irradiation with radiation is detected.

When sensing a radiation image, charges converted from radiation may be trapped in a dangling bond of a semiconductor layer of a conversion element, a defect, or the like and remain in the conversion element after image sensing. If charges generated by preceding image sensing remain in the conversion element, the remaining charges can be released in succeeding image sensing to decrease the detection accuracy of an incident radiation dose. As the interval between image sensing operations is shorter in sensing a radiation image, the influence of remaining charges can become more serious.

The present invention has as its object to provide a technique of improving the detection accuracy of the dose of radiation entering a radiation image sensing apparatus.

SUMMARY OF THE INVENTION

According to some embodiments, a radiation image sensing apparatus comprising an image sensing area where a plurality of conversion elements are arranged and used in an image sensing operation of acquiring a radiation image corresponding to incidence of radiation, a detection element configured to detect a radiation dose of radiation entering the image sensing area, a readout unit, and a control unit, wherein the control unit corrects a detection signal read out from the detection element by the readout unit during incidence of radiation in a second image sensing operation performed next to a first image sensing operation, based on a correction amount acquired based on a correction signal read out from the detection element by the readout unit after an end of the incidence of the radiation in the first image sensing operation, and detects a dose of incident radiation in the second image sensing operation based on the corrected detection signal, is provided.

According to some other embodiments, a control method for a radiation image sensing apparatus including an image sensing area where a plurality of conversion elements are arranged and used in an image sensing operation of acquiring a radiation image corresponding to incidence of radiation, a detection element configured to detect radiation entering the image sensing area, and a readout unit, the method characterized by comprising: a first step of acquiring a correction signal read out from the detection element by the readout unit after an end of incidence of radiation in a first image sensing operation; a second step of reading out a detection signal from the detection element by the readout unit during the incidence of the radiation in a second image sensing operation performed next to the first step; and a third step of correcting the detection signal in accordance with a correction amount based on the correction signal, and detecting an incident radiation dose based on the corrected detection signal, is provided.

According to still other embodiments, a non-transitory computer-readable storage medium storing a program for causing a computer to execute a control method for a radiation image sensing apparatus including an image sensing area where a plurality of conversion elements are arranged and used in an image sensing operation of acquiring a radiation image corresponding to incidence of radiation, a detection element configured to detect radiation entering the image sensing area, and a readout unit, the method characterized by comprising: a first step of acquiring a correction signal read out from the detection element by the readout unit after an end of incidence of radiation in a first image sensing operation; a second step of reading out a detection signal from the detection element by the readout unit during the incidence of the radiation in a second image sensing operation performed next to the first step; and a third step of correcting the detection signal in accordance with a correction amount based on the correction signal, and detecting an incident radiation dose based on the corrected detection signal, is provided.

Further features of the present invention will become apparent from the following description of exemplary embodiments with reference to the attached drawings.

BRIEF DESCRIPTION OF THE DRAWINGS

The accompanying drawings, which are incorporated in and constitute a part of the specification, illustrate presently preferred embodiments of the invention, and together with the general description given above and the detailed description of the preferred embodiments given below, serve to explain the principles of the invention.

FIG. 4 is a graph showing a correction amount determination method for the radiation image sensing apparatus in FIG. 1A.

FIG. 5 is a graph showing a correction amount determination method for the radiation image sensing apparatus in FIG. 1A.

FIG. 6B is a flowchart showing the operation of the radiation image sensing apparatus in FIG. 1A.

DESCRIPTION OF THE EMBODIMENTS

Concrete embodiments of a radiation image sensing apparatus according to the present invention will be described with reference to the accompanying drawings. Note that radiation according to the present invention can include not only α-rays, β-rays, and γ-rays that are beams generated by particles (including photons) emitted by radioactive decay but also beams having energy equal to or higher than the energy of these beams, for example, X-rays, particle beams, and cosmic rays.

Figure 1A:
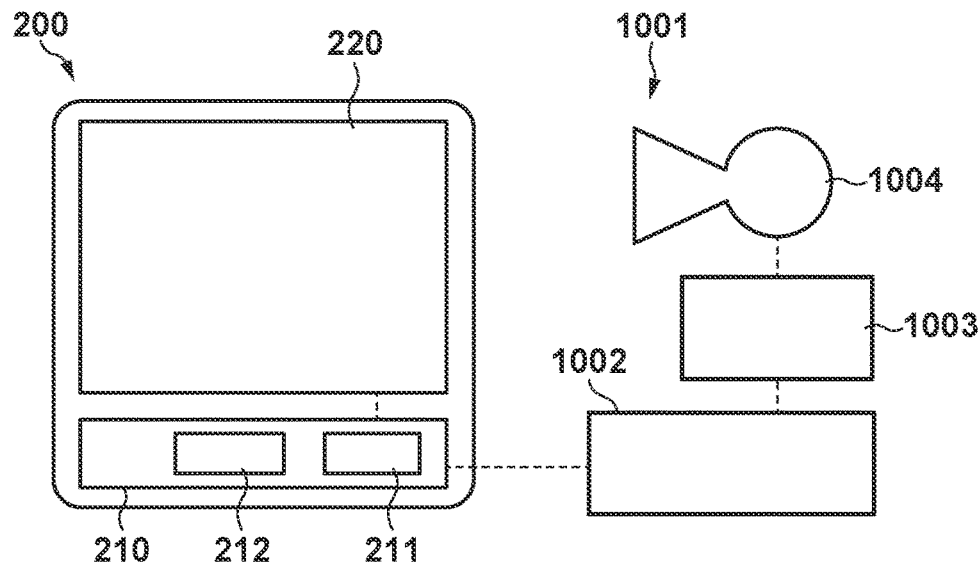
FIG. 1A is a block diagram showing an example of the arrangement of a system using a radiation image sensing apparatus according to an embodiment of the present invention.

The arrangement of a radiation image sensing apparatus according to an embodiment of the present invention will be described with reference to FIGS. 1A to 5. FIG. 1A is a block diagram showing an example of the arrangement of a system 1001 using a radiation image sensing apparatus 200 according to the first embodiment of the present invention. The system 1001 includes the radiation image sensing apparatus 200, a control system 1002, a radiation interface 1003, and a radiation source 1004. The control system 1002 can control the overall system 1001. A user uses the control system 1002 to input image sensing conditions and the like for acquiring a radiation image. The user may select image sensing conditions properly from a recipe stored in advance in, for example, a memory mounted in the control system 1002 or input them individually. When the user pushes an exposure switch attached to the control system 1002, the control system 1002 outputs a signal to the radiation source 1004 via the radiation interface 1003 to start exposure to radiation. In accordance with this signal, the radiation source 1004 irradiates the radiation image sensing apparatus 200 with radiation via an object (not shown). The radiation source 1004 stops the irradiation with radiation in accordance with a signal from the control system 1002 to stop the exposure. The radiation image sensing apparatus 200 includes a control unit 210 and a signal detection unit 220.

The control unit 210 supplies a control signal to the signal detection unit 220 and controls the respective constituent elements of the radiation image sensing apparatus 200. The control unit 210 can include, for example, a CPU (Central Processing Unit) 211 that executes a program for controlling the signal detection unit 220, and a memory 212 in which a program for performing an image sensing operation is saved. For example, the control unit 210 may be constituted by a PLD (Programmable Logic Device) such as a FPGA (Field Programmable Gate Array). For example, the control unit 210 may be constituted by an ASIC (Application Specific Integrated Circuit) or a general-purpose computer in which a program is installed. The control unit 210 may be constituted by a combination of all or some of these components. The operation of the signal detection unit 220 may be controlled not only by the control unit 210, but some control operations may also be performed by the control system 1002.

Figure 1B:
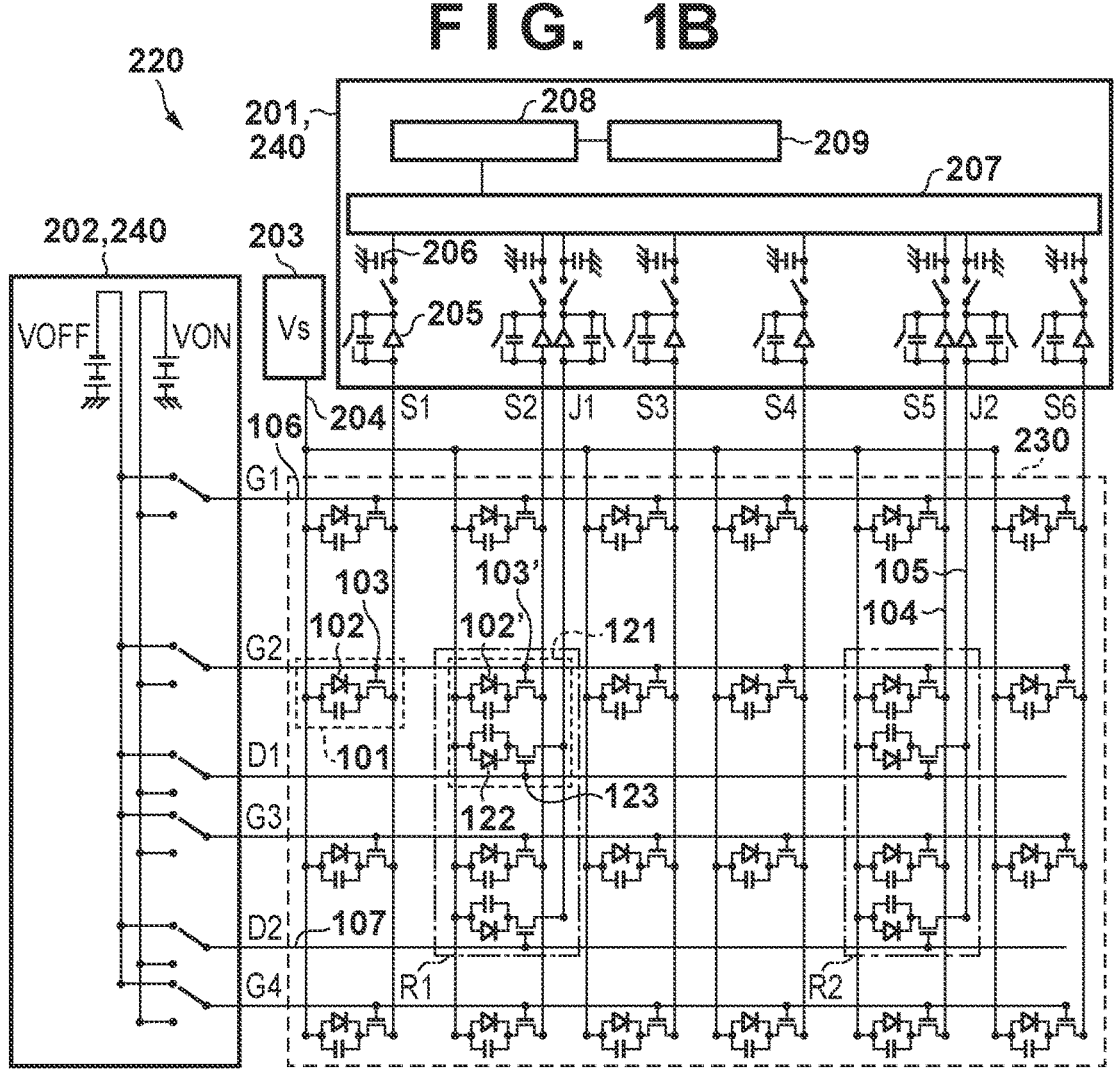
FIG. 1B is a circuit diagram showing an example of the circuit arrangement of the detection unit of the radiation image sensing apparatus according to the embodiment of the present invention.

FIG. 1B is an equivalent circuit diagram showing the circuit arrangement of the signal detection unit 220 of the radiation image sensing apparatus 200. The signal detection unit 220 includes a readout circuit 201, a driving circuit 202, a bias power supply 203, and an image sensing area 230 where pixels 101 and 121 are arranged. The readout circuit 201 and the driving circuit 202 cooperate with each other and function as a readout unit 240 that reads out signals from the pixels 101 and 121 in accordance with a control signal from the control unit 210. In the arrangement shown in FIG. 1B, 4 (rows)×6 (columns) pixels 101 and 121 are provided in the image sensing area 230 for acquiring a radiation image. However, the number of pixels 101 and 121 arranged in the image sensing area 230 is not limited to this example. For example, 100 (rows)×30 (columns) pixels 101 and 121 may be arranged or 2,000 (rows)×2,000 (columns) pixels 101 and 121 may be arranged.

In this embodiment, the image sensing area 230 includes the pixels 101 that output an image signal for generating a radiation image, and the pixels 121 that output an image signal for generating a radiation image and output a detection signal for detecting the radiation dose of incident radiation. Each pixel 101 includes a conversion element 102 that generates an image signal serving as an electrical signal corresponding to incident radiation, and a switching element 103. The conversion elements 102 of the respective pixels 101 are connected to signal lines 104 (S1 to S6) via the switching elements 103, and signals output from the pixels 101 are input to the readout circuit 201 via the signal lines 104. Each pixel 121 includes a conversion element 102' that outputs an image signal for generating a radiation image, a switching element 103', a detection element 122 that detects the radiation dose of incident radiation, and a switching element 123. The conversion elements 102' of the respective pixels 121 are connected to the signal lines 104 (S2 and S5) via the switching elements 103', and signals output from the conversion elements 102' of the pixels 121 are input to the readout circuit 201 via the signal lines 104. The detection elements 122 of the respective pixels 121 are connected to detection lines 105 (J1 and J2) via the switching elements 123, and signals output from the detection elements 122 of the pixels 121 are input to the readout circuit 201 via the detection lines 105. That is, the image sensing area 230 includes the conversion elements 102 and 102' used in an image sensing operation of acquiring a radiation image corresponding to incidence of radiation, and the detection elements 122 that detect the radiation dose of radiation entering the image sensing area 230. In this embodiment, the detection elements 122 of the pixels 121 are arranged in the image sensing area 230 where the conversion elements 102 (pixels 101) are arranged. However, the arrangement of the pixels 121 is not limited to this. For example, the detection elements 122 may be arranged outside the image sensing area 230 along the periphery of the image sensing area 230.

In the arrangement shown in FIG. 1B, regions of interest (ROI) for detecting the radiation dose of incident radiation are provided at two portions R1 and R2. The two pixels 121 are arranged in each ROI. Charges generated in the detection element 122 by incidence of radiation can be read out via the switching element 123 and the detection line 105 to acquire the radiation dose of the radiation entering the ROI. Although ROIs are arranged at two portions in this embodiment, the number of ROIs and their arrangement are not limited to this. For example, ROIs may be provided at 5×5=25 portions or 10×10=100 portions. Also, ROIs may be arranged in the image sensing area 230 evenly or unevenly particularly in a region of high interest. The number of pixels 121 (detection elements 122) included in one ROI is not limited to two and may be one or three or more. It suffices to arrange at least one pixel 121 including the detection element 122 in the signal detection unit 220 of the radiation image sensing apparatus 200.

The pixels 101 and 121 are connected to a common bias line 204 and receive a predetermined bias voltage from the bias power supply 203. The gate electrodes of the respective switching elements 103 and 103' are connected to gate lines 106 (G1 to G4). The driving circuit 202 of the readout unit 240 switches a voltage input to the gate electrodes of the switching elements 103 and 103'. When the switching elements 103 and 103' are turned on (conductive), the signals of the conversion elements 102 and 102' are output to the readout circuit 201 of the readout unit 240. The gate electrodes of the respective switching elements 123 are connected to gate lines 107 (D1 and D2). The driving circuit 202 of the readout unit 240 switches a voltage input to the gate electrodes of the switching elements 123. When the switching elements 123 are turned on (conductive), the signals of the detection elements 122 are output to the readout circuit 201 of the readout unit 240. In this specification, as described above, a line of the pixels 101 and 121 in a direction in which the signal line 104 runs will be called a column, and a line of the pixels 101 and 121 in a direction (a direction in which the gate lines 106 and 107 run) crossing (perpendicular to) this direction will be called a row.

The readout circuit 201 includes operational amplifiers (amplifiers) 205, sample-and-hold circuits (SH) 206, a multiplexer (MUX) 207, an A/D converter (ADC) 208, and a signal processor 209. Each of the signal line 104 and detection line 105 is connected to the input terminal of the operational amplifier 205 and one terminal of a feedback capacitance. The other terminal of the feedback capacitance is connected to the output terminal of the operational amplifier 205. The output terminal of the operational amplifier 205 is connected to the ADC 208 via the sample-and-hold circuit 206 and the MUX 207. Signals output from the pixels 101 and 121 are digitally converted. The signal processor 209 performs various processes on the digitally converted signals.

The conversion elements 102, 102', and 122 can be, for example, photoelectric conversion elements such as PIN photodiodes. When radiation enters the image sensing area 230, it is converted by a scintillator (not shown) into light that can be sensed by the conversion elements 102, 102', and 122. The detection elements 122 are exposed to the converted light. Then, electrons and holes generated in the semiconductor layer of the detection elements 122 are read by an applied electric field. That is, electrons and holes are transported to the electrodes by a potential difference between potentials applied from the bias power supply 203 and the readout circuit 201. The charges are read out in real time by the readout circuit 201, acquiring the irradiation information of the radiation. The amplifier according to this embodiment is, for example, a charge readout amplifier in the above description, but may be of a current readout or voltage readout amplifier.

Figure 2A:
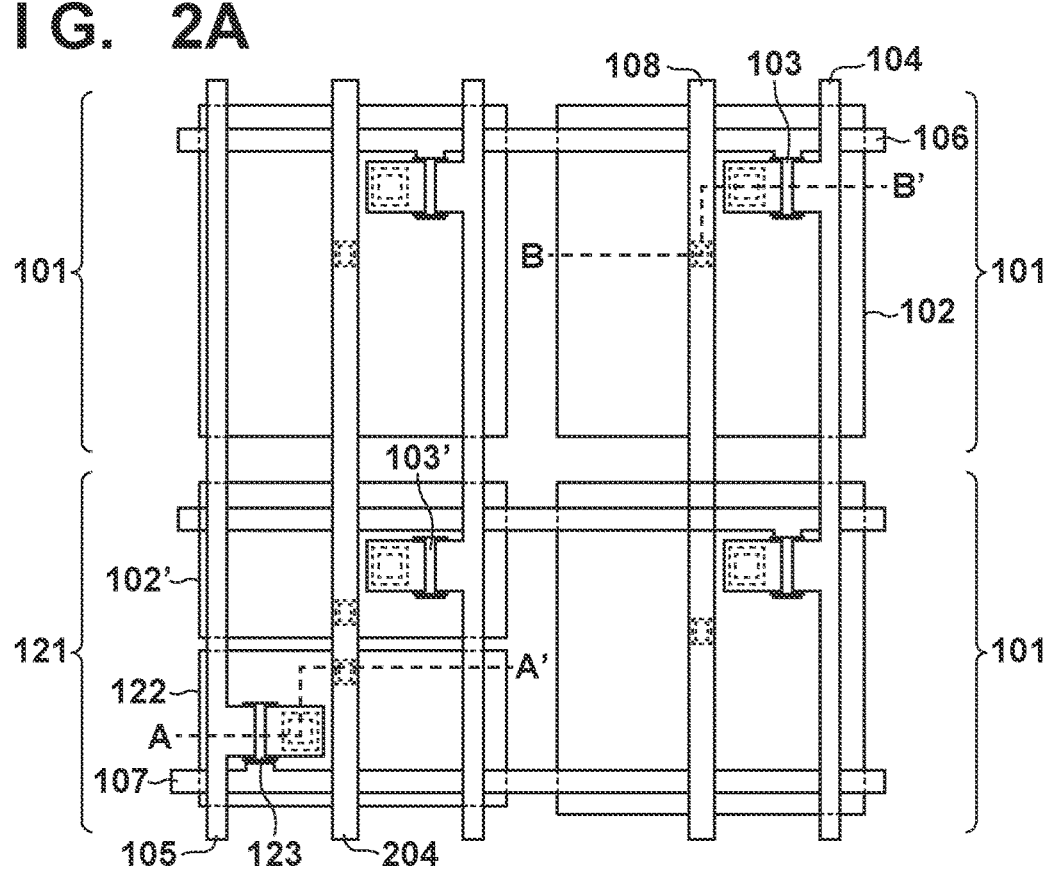
FIG. 2A is a plan view of the pixels of the radiation image sensing apparatus in FIG. 1A.
Figure 2B:
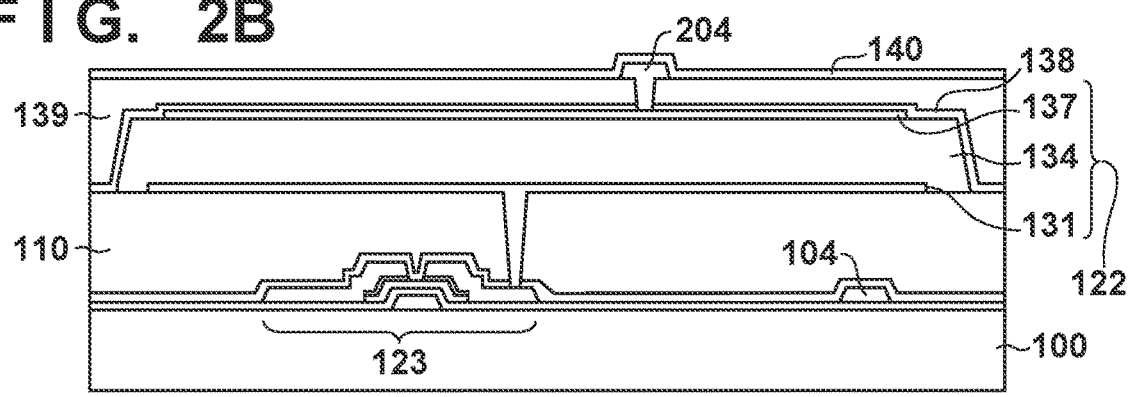
FIG. 2B is a sectional view of the pixels of the radiation image sensing apparatus in FIG. 1A.
Figure 2C:
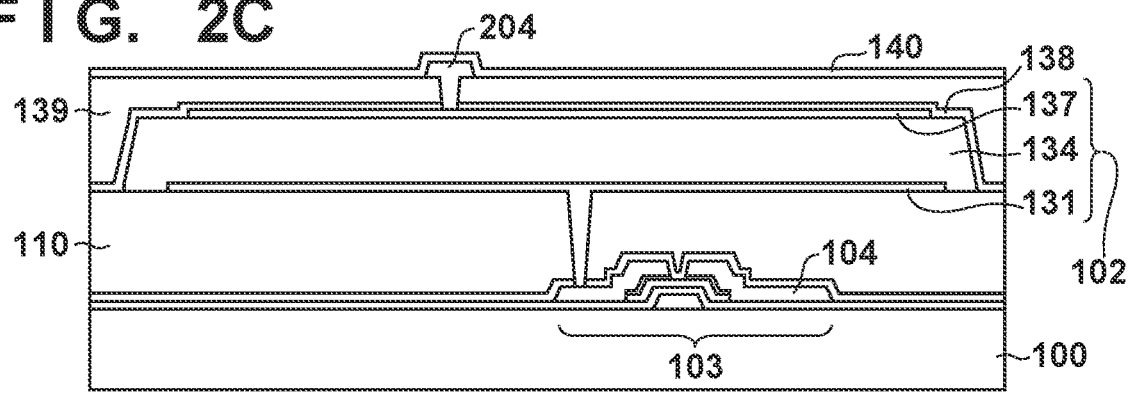
FIG. 2C is a sectional view of the pixels of the radiation image sensing apparatus in FIG. 1A.

Next, the structures of the pixels 101 and 121 will be described with reference to FIGS. 2A to 2C. FIG. 2A is a plan view of the pixels 101 and 121. The arrangement shown in FIG. 2A represents an example in which three pixels 101 and one pixel 121 are arrayed. FIG. 2B is a sectional view taken along A-A' in FIG. 2A. FIG. 2C is a sectional view taken along B-B' in FIG. 2A.

As shown in FIGS. 2A and 2B, the pixel 121 includes the detection element 122 and the switching element 123. A signal can be acquired from the detection element 122 at high accuracy when the switching element 123 is arranged with respect to the detection element 122 of the pixel 121. However, even when no switching element 123 is arranged, the irradiation information of radiation can be acquired. In this embodiment, the detection element 122 includes a PIN photodiode 134 serving as a converter for obtaining an electrical signal from radiation. The detection element 122 is connected to the detection line 105 via the switching element 123.

The detection element 122 is stacked via an interlayer insulation layer 110 on the switching element 123 using a thin-film transistor (TFT) that is provided on an insulating support substrate 100 such as a glass substrate. The detection element 122 includes an electrode 131, the PIN photodiode 134, and an electrode 137. A protection film 138, an interlayer insulation layer 139, the bias line 204, and a protection film 140 are arranged in order on the detection element 122. A planarizing film and scintillator (neither is shown) are arranged on the protection film 140. The electrode 137 is connected to the bias line 204 through a via formed in a contact hole.

As shown in FIGS. 2A and 2C, the pixel 101 includes the conversion element 102 and the switching element 103. The PIN photodiode 134 is arranged in the conversion element 102, similar to the detection element 122. The conversion element 102 is connected to the signal line 104 via the switching element 103. The structures of the conversion element 102 and switching element 103 may be the same as those of the detection element 122 and switching element 123 except for the size of the PIN photodiode 134 (the area of the PIN photodiode 134 on an orthogonal projection to the image sensing area 230), and a description of these structures will not be repeated. This also applies to the conversion element 102' and switching element 103' in the pixel 121.

Although PIN photodiodes are used as the conversion elements 102 and 102' and the detection element 122 in this embodiment, the present invention is not limited to this. For example, MIS sensors may be used as the conversion elements 102 and 102' and the detection element 122. For example, the conversion element 102' for generating an image signal and the detection element 122 for generating a detection signal are arranged in the pixel 121. However, only the detection element 122 may be arranged without arranging the conversion element 102'. The loss of an image signal due to the absence of the conversion element 102' can be corrected using image signals output from the pixels 101 arranged around the pixel 121. The switching elements 103, 103', and 123 are inverted-staggered TFTs arranged on the insulating support substrate 100 in this embodiment, but may be, for example, transistors formed on the support substrate 100 of silicon or the like.

Figure 3:
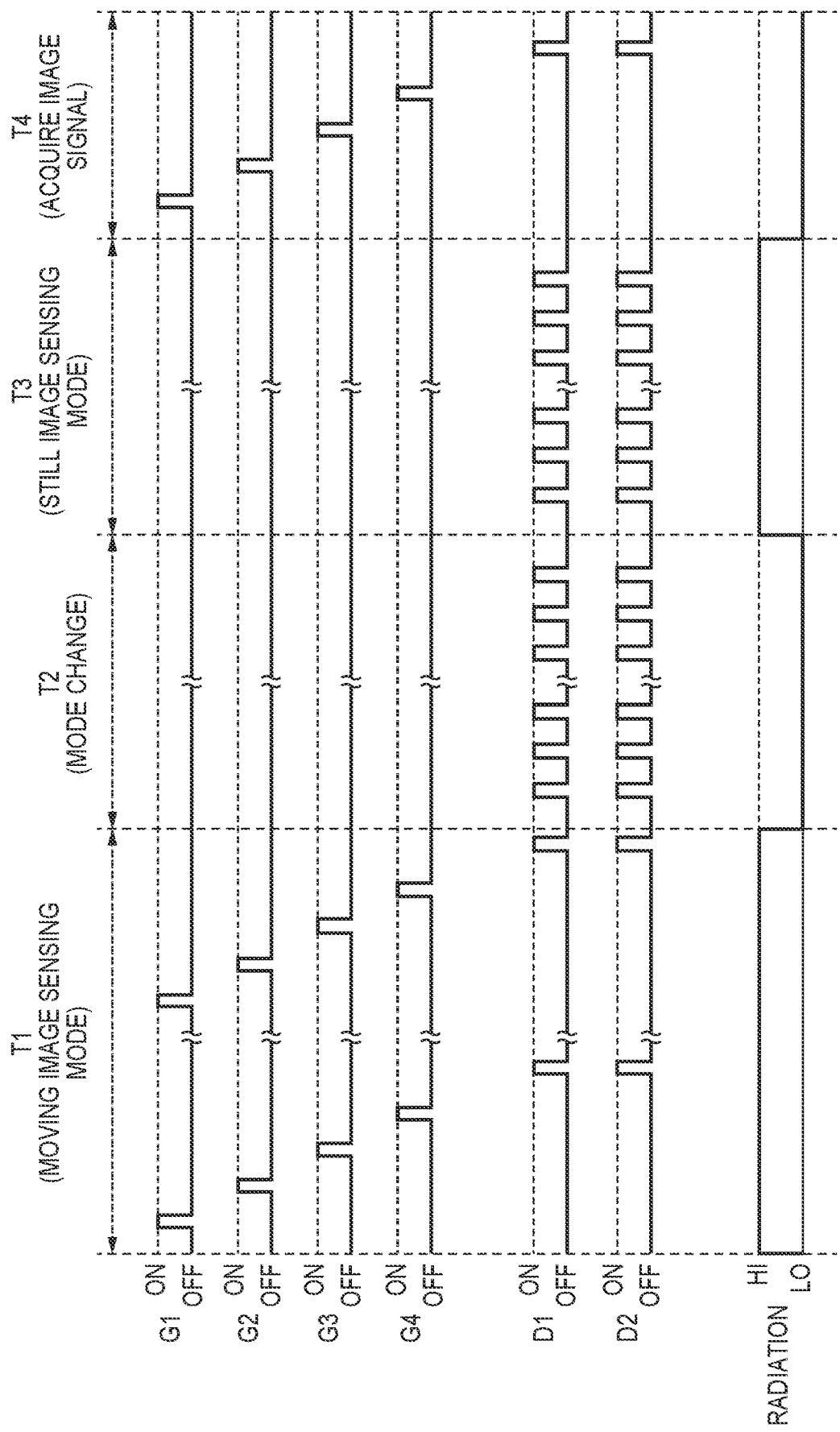
FIG. 3 is a timing chart showing the operation of the radiation image sensing apparatus in FIG. 1A.

Next, the operation of the radiation image sensing apparatus 200 will be described with reference to FIG. 3. In FIG. 3, for descriptive convenience, ON represents a voltage at which the switching elements 103, 103', and 123 connected to the respective gate lines 106 (G1 to G4) and 107 (D1 and D2) are turned on (conductive), and OFF represents a voltage at which they are turned off (nonconductive). "Radiation" is incident at HI and not incident at LO. In the chart shown in FIG. 3, a mode (period T1) in which a moving image is sensed is switched via a mode change (period T2) to a mode in which a still image is sensed. In the mode (periods T3 and T4) in which a still image is sensed, automatic exposure control (AEC) is executed. However, the control of the operation of the radiation image sensing apparatus 200 according to this embodiment is not limited to this. For example, the operation according to this embodiment is applicable even when AEC is executed in a situation in which still images are successively sensed using radiation of different energies in order to acquire an energy subtraction image. For example, the operation according to this embodiment may be applied when AEC is executed to change an object after preceding image sensing and then sense an image of another object. Also, the operation according to this embodiment may be applied in various situations in which charges generated by preceding image sensing readily remain in the detection element 122 and an afterimage arising from the remaining charges causes a problem when, for example, AEC is executed to sense an image after high-dose image sensing. In this manner, the operation according to this embodiment may be applied to image sensing in which image sensing conditions are different between a preceding image sensing operation and a succeeding image sensing operation. In addition, the operation according to this embodiment may be applied when still images are sensed successively under the same image sensing conditions while executing AEC.

Although the radiation image sensing apparatus 200 executes AEC as exposure control in this embodiment, the present invention is not limited to this. It is also possible to apply the radiation image sensing apparatus 200 to measurement (monitoring) of a radiation dose used in AEC and control the radiation image sensing apparatus 200 by a control unit arranged outside the radiation image sensing apparatus 200. A control method for the radiation image sensing apparatus 200, which will be described below, may be applied as exposure control not only to AEC, but also to a radiation irradiation start automatic detection technique of detecting the start of irradiation with radiation. For example, this control method may be applied to a radiation irradiation end automatic detection technique of detecting the end of irradiation with radiation.

First, an operation in the period T1 of FIG. 3 will be explained. The period T1 is a period in which an image of an object is sensed in the mode of an image sensing operation of sensing a moving image. In the period T1, the object is kept irradiated with radiation, and image signals generated in the pixels 101 and 121 are acquired repetitively. The radiation is emitted continuously in the chart shown in FIG. 3, but may be emitted as pulses. An operation of removing a dark current generated in the conversion elements 102 and 102' and the detection elements 122 may be performed before the period T1, in other words, before the start of exposure to the radiation. More specifically, the control unit 210 controls the readout unit 240 (the readout circuit 201 and the driving circuit 202) to reset the conversion elements 102 and 102' and the detection elements 122 periodically to a constant potential.

Next, an operation in the period T2 will be explained. The period T2 is a mode change period in which the operation shifts from preceding image sensing to succeeding image sensing and the irradiation with radiation is stopped. That is, the period T2 is a period after the end of incidence of the radiation in the period T1. In the period T2, the control unit 210 acquires correction signals that are generated by the detection elements 122 in preceding image sensing to correct an afterimage arising from the emission of remaining charges when executing AEC in image sensing in the period T3.

Image sensing is sometimes performed a plurality of times at a short interval when, for example, a doctor wants to sense a still image quickly while checking a moving image sensed by the radiation image sensing apparatus 200, or when one image is obtained from a difference between still images, like an energy subtraction image. In this embodiment, the operation in the period T2 for acquiring a correction signal is executed in response to the end of the image sensing operation in the period T1 in order to shorten the time between image sensing operations.

More specifically, the gate lines 107 (D1 and D2) are reset, and the control unit 210 controls the readout unit 240 (the readout circuit 201 and the driving circuit 202) to acquire outputs when the gate lines 107 are at the OFF voltage. Then, the ON voltage is applied to the gate lines 107 (D1 and D2), and the control unit 210 acquires outputs when the gate lines 107 are ON, that is, outputs from the detection elements 122. The control unit 210 can acquire a correction signal by subtracting an output when the gate line 107 is OFF from an output when the gate line 107 is ON. The duration of the period T2 can greatly change depending on the method, conditions, and the like used in performing the image sensing operation. Even so, the control unit 210 needs to acquire at least one correction signal during the period T2.

Next, the period T3 will be explained. In the period T3, the control unit 210 controls the driving circuit 202 to always apply the OFF voltage to the gate lines 106 (G1 to G4) during the incidence of radiation. The switching elements 103 and 103' are thus turned off, and charges corresponding to the incident radiation are generated and accumulated in the conversion elements 102 and 102'. At the same time, the control unit 210 controls the readout unit 240 (the readout circuit 201 and the driving circuit 202) to repetitively read detection signals corresponding to the charges accumulated in the detection elements 122 during the incidence of radiation. Accordingly, the dose of radiation entering the detection elements 122 is monitored at any time during the incidence of the radiation. More specifically, the ON voltage is applied to the gate lines 107 (D1 and D2), and the control unit 210 acquires outputs when the gate lines 107 are ON, that is, outputs from the detection elements 122. The control unit 210 can acquire a detection signal by subtracting an output when the gate line 107 is OFF from an output when the gate line 107 is ON. The control unit 210 repeats the operation of acquiring a detection signal.

When an afterimage arising from the emission of remaining charges generated in preceding image sensing is superposed in the acquired detection signal, no incident radiation dose can be monitored accurately and the AEC accuracy decreases. To solve this problem, the control unit 210 corrects the detection signal in accordance with a correction amount based on the correction signal acquired in the period T2.

When only one correction signal is acquired in the period T2, the control unit 210 may determine the signal value of this correction signal as the correction amount and perform correction to subtract the correction amount from the signal value of the detection signal acquired in the period T3. For example, the control unit 210 may apply a preset coefficient to the signal value of the correction signal and determine the resultant correction signal as the correction amount. When the control unit 210 controls the readout unit 240 (the readout circuit 201 and the driving circuit 202) to read out a plurality of correction signals, and acquires these correction signals, it generates a correction function corresponding to the correction signals acquired in the period T2, as shown in FIG. 4. Based on this correction function, the control unit 210 may determine a correction amount that can be generated at a timing when each detection signal is acquired in the period T3, and correct the detection signal acquired in the period T3. When the control unit 210 acquires a plurality of correction signals in the period T2, it may determine a correction amount based on the average value of the correction signals, as shown in FIG. 5. The correction amount can be selected appropriately in accordance with the situation.

The control unit 210 detects a radiation dose in real time based on the corrected detection signals, and acquires the integrated dose of incident radiation based on the radiation dose. In accordance with the integrated dose, the control unit 210 determines whether to stop exposure to the radiation. In accordance with the determination result, the control unit 210 outputs a signal for stopping the exposure to the radiation. For example, when the control unit 210 determines that the integrated dose of the radiation has reached a predetermined value, it may output a signal for stopping the exposure. For example, the control unit 210 may acquire, from a temporal change of the integrated dose of the radiation, the time when the integrated dose reaches a predetermined value, and may output a signal for stopping the exposure in accordance with the time. The signal output from the control unit 210 to stop the exposure to the radiation is input to the radiation source 1004 via the control system 1002 and the radiation interface 1003, and the radiation source 1004 stops the irradiation with the radiation. After outputting the signal for stopping the exposure to the radiation, the control unit 210 shifts to the period T4 and controls the readout unit 240 (the readout circuit 201 and the driving circuit 202) to read out an image signal.

In the period T2, if the control unit 210 determines that the correction signal has a signal value that need not be corrected in executing AEC in the period T3, it may stop the driving for acquiring a correction signal by the readout unit 240. After stopping the acquisition of the correction signal, the control unit 210 may reset the conversion elements 102 and 102', the detection elements 122, the signal lines 104, and the detection lines 105 before exposure to radiation via the readout unit 240 (the readout circuit 201 and the driving circuit 202) till the period T3. For example, after stopping the acquisition of the correction signal, the control unit 210 may output a signal to request the start of exposure in order to shift to the period T3.

In the period T2, if the control unit 210 acquires a plurality of correction signals and determines that the value of an initially acquired correction signal is less reliable, it may exclude the initial correction signal in determining a correction amount. The correction amount may be determined using signals except some of acquired correction signals, for example, one or several correction signals initially acquired among a plurality of correction signals. For example, the correction amount may be determined using signals acquired later among a plurality of correction signals.

Driving conditions of the detection elements 122 in the periods T2 and T3 may be similar to each other, as shown in FIG. 3, in order to improve the correction accuracy of the detection signal in executing AEC in the period T3. For example, the control unit 210 may control the readout unit 240 (the readout circuit 201 and the driving circuit 202) to read out correction signals and detection signals from the detection elements 122 in the same charge accumulation time. For example, the control unit 210 may control the readout unit 240 (the readout circuit 201 and the driving circuit 202) to read out a plurality of correction signals and a plurality of detection signals in the same sampling cycle. The time in which correction signals are acquired can be shortened by acquiring correction signals by the control unit 210 under the same conditions as those of the AEC operation because the AEC operation of detecting a radiation dose in real time needs to be quick. Even when the time between image sensing operations is short, the control unit 210 can acquire correction signals and improve the radiation dose detection accuracy and the AEC accuracy.

Next, the period T4 will be explained. The period T4 is a period in which image signals accumulated in the conversion elements 102 and 102' by the incidence of radiation after the irradiation with the radiation are read out in an image sensing operation of sensing a still image. In the period T4, the control unit 210 controls the driving circuit 202 to apply the OFF voltage to the gate lines 107 (D1 and D2). In addition, the control unit 210 controls the driving circuit 202 to sequentially apply the ON voltage to the gate lines 106 (G1 to G4), and transfers image signals accumulated in the conversion elements 102 and 102' to the readout circuit 201 via the signal lines 104. The image signals are used as, for example, signals of a radiation image used in medical diagnosis. The conversion elements 102 and 102' are different in the area of the PIN photodiode that performs photoelectric conversion. Even if radiation doses entering the conversion elements 102 and 102' are equal, the signal values of output image signals are different. However, these signals undergo proper correction such as white correction or gain adjustment in the signal processor 209 or the like, and can be used as image signals for generating a radiation image.

Figure 6A:
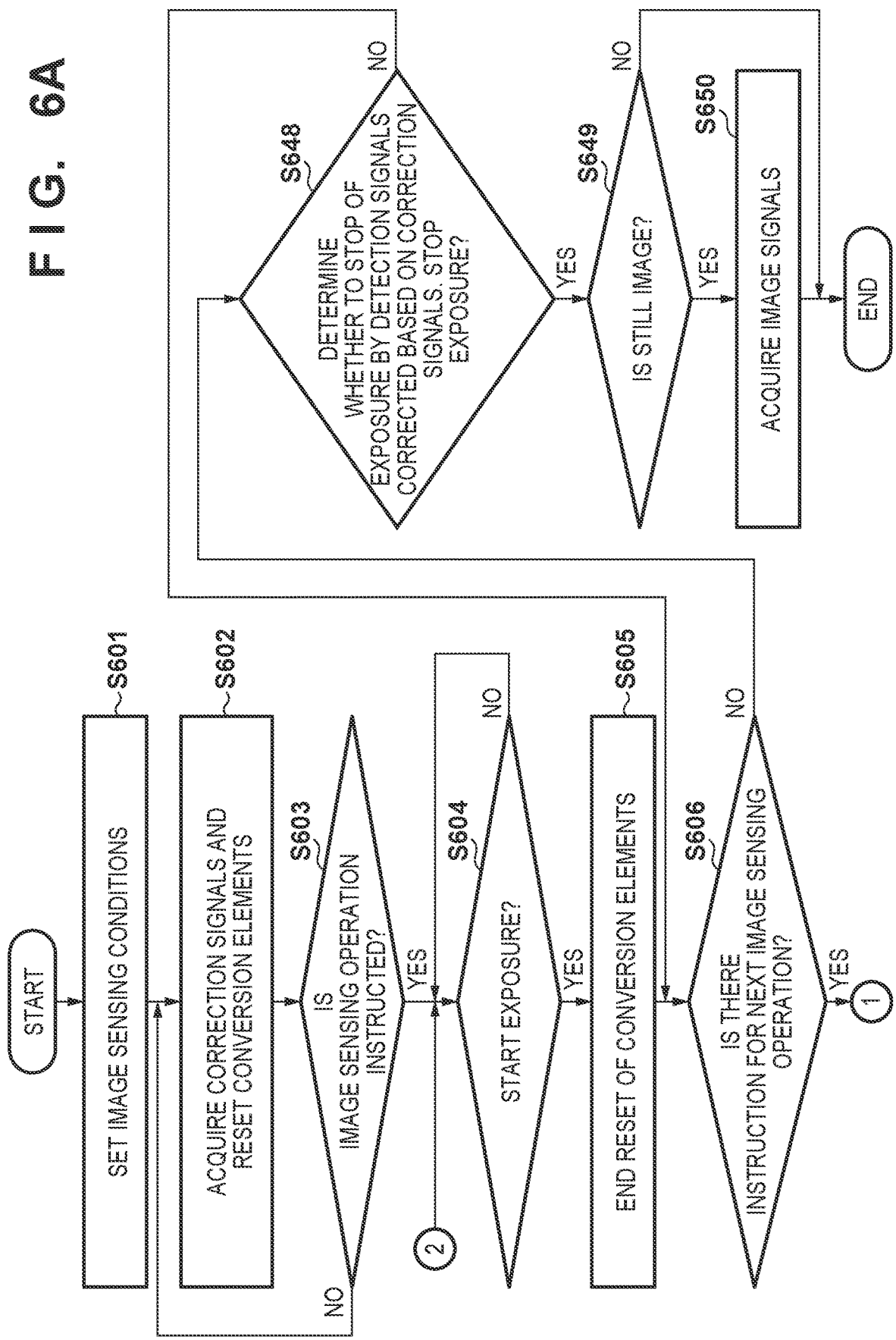
FIG. 6A is a flowchart showing the operation of the radiation image sensing apparatus in FIG. 1A.

FIGS. 6A and 6B are flowcharts for explaining the operation of the radiation image sensing apparatus 200. In step S601, the control unit 210 acquires image sensing information of image sensing that is input to the control system 1002 by a user such as a doctor or a radiographer, and sets image sensing conditions under which a moving image or a still image is sensed. For example, the control unit 210 sets the image sensing conditions by reading out, from the memory 212 to the CPU 211, an operation program suited to the image sensing information input to the control system 1002. After setting the image sensing conditions, the control unit 210 advances to step S602 and performs the operation in the above-described period T2 in order to acquire correction signals used in executing AEC in the first image sensing operation. At this time, the control unit 210 may control the readout unit 240 (the readout circuit 201 and the driving circuit 202) to perform a reset operation of removing a dark current from the conversion elements 102 and 102' for acquiring a radiation image. If an instruction for an image sensing operation is input in step S603 by, for example, pressing an exposure switch by the user, the control unit 210 advances to step S604 and determines whether to start exposure. The control unit 210 may determine the start of exposure, by simultaneously receiving an exposure start signal output from the control system 1002 to the radiation source 1004. Alternatively, the control unit 210 may control the detection elements 122 to output detection signals, and may determine the start of irradiation with radiation, based on the detection signals corrected in accordance with a correction amount based on the correction signals. If the control unit 210 detects the start of irradiation with radiation in step S604, it advances to step S605, ends the reset operation of the conversion elements 102 and 102', and starts the image sensing operation. At the same time, the control unit 210 controls the detection elements 122 to output detection signals, detects the dose of radiation entering the detection elements 122 in real time based on the correction signals, and acquires the integrated dose of the incident radiation.

After the start of the image sensing operation, the control unit 210 checks in step S606 whether there is an instruction for an image sensing operation next to the current image sensing operation. The case in which there is an instruction for the next image sensing operation is, for example, a case in which the user has input (designated) successive execution of a plurality of image sensing operations to the control system 1002 when the control unit 210 acquires in step S601 the image sensing information input to the control system 1002. This is equivalent to, for example, a case in which, before the period T1 shown in FIG. 3, the user has designated image sensing operations including an image sensing operation starting from the period T1 and an image sensing operation starting from the period T3. Also, the case in which there is an instruction for the next image sensing operation can be, for example, a case in which the user has input (designated), to the control system 1002 during the current image sensing operation, an image sensing operation to be performed successively to the current image sensing operation. This is equivalent to, for example, a case in which the user designates an image sensing operation starting from the period T3 during the period T1 shown in FIG. 3.

If the control unit 210 determines in step S606 that there is an instruction for the next image sensing operation, it determines in step S607 whether the image sensing conditions are equal or different between the current and next image sensing operations. If the image sensing operation is performed successively under image sensing conditions different between the current and next image sensing operations, the control unit 210 advances to step S608. If the image sensing operation is performed successively under image sensing conditions equal between the current and next image sensing operations, the control unit 210 advances to step S628. In step S608, the control unit 210 determines whether exposure to the radiation is to be stopped in accordance with the integrated dose of the radiation entering the detection elements 122 based on the detection signals corrected by the correction amount based on the correction signals, as represented in the above-described period T3. In accordance with the result of the exposure stop determination, the control unit 210 outputs a signal for stopping the exposure to the radiation. For example, when the control unit 210 determines that the integrated dose of the radiation has reached a predetermined value, it may output a signal for stopping the exposure. For example, the control unit 210 may acquire, from a temporal change of the integrated dose of the radiation, the time when the integrated dose reaches a predetermined value, and output a signal for stopping the exposure in accordance with the time. The signal output from the control unit 210 to stop the exposure to the radiation is input to the radiation source 1004 via the control system 1002 and the radiation interface 1003, and the radiation source 1004 stops the irradiation with the radiation. After outputting the signal for stopping the exposure to the radiation, if the control unit 210 determines in step S609 that the image sensing operation performed until now is an image sensing operation of sensing a still image, it advances to step S610. Step S610 can be the operation in the above-described period T4. The control unit 210 controls the readout unit 240 (the readout circuit 201 and the driving circuit 202) to read out image signals from the conversion elements 102 and 102'. The control unit 210 acquires the image signals, shifts to step S611 in response to the end of the image sensing operation, and performs acquisition of correction signals represented in the above-described period T2. Image sensing conditions for performing an image sensing operation different from the preceding image sensing operation are set at the same time as acquiring the correction signals. For example, the mode is changed from the moving image sensing mode to the still image sensing mode. After acquiring the correction signals and setting the image sensing conditions, the control unit 210 returns to step S604 and determines whether to start exposure for the next image sensing operation. If the start of exposure is detected, the control unit 210 starts the next image sensing operation. If the control unit 210 determines in step S609 that the image sensing operation performed until now is an image sensing operation of sensing a moving image, image signals have already been acquired, as represented in the period T1 of FIG. 3. Thus, the control unit 210 determines that the image sensing operation has ended, and shifts to step S611 in response to this.

If the control unit 210 determines in step S607 that the image sensing conditions are equal between the current and next image sensing operations, it advances to step S628. In steps S628 to S630, the control unit 210 performs the same control as that in steps S608 to S610. Since the image sensing conditions of the preceding and succeeding image sensing operations are equal, the control unit 210 acquires correction signals in step S631 without setting image sensing conditions. After acquiring the correction signals in step S631, the control unit 210 returns to step S604 and determines whether to start exposure for the next image sensing operation. After detecting the start of exposure, the control unit 210 starts the next image sensing operation.

If the control unit 210 determines in step S606 that there is no instruction for the next image sensing operation, it shifts to step S648 and determines whether to stop exposure to the radiation in accordance with the integrateddose of the radiation entering the detection elements 122 based on the detection signals corrected by the correction amount based on the correction signals. In accordance with the result of the exposure stop determination, the control unit 210 outputs a signal for stopping the exposure to the radiation. Until the control unit 210 outputs the signal for stopping the exposure to the radiation, it returns to step S606 and checks whether there is an instruction for an image sensing operation next to the current image sensing operation. If the user inputs the instruction for the next image sensing operation to the control system 1002, the control unit 210 shifts to step S607 and continues the image sensing operation. If there is no instruction for the next image sensing operation and the control unit 210 determines that the integrated dose of the radiation has reached a predetermined value, the control unit 210 outputs a signal for stopping the exposure to the radiation, and shifts to step S649. In steps S649 and S650, the control unit 210 performs the same control as that in steps S609 and S610 described above.

In the above description, the control unit 210 outputs in step S608 (S628 or S648) a signal for stopping the exposure to the radiation, in accordance with the result of the exposure stop determination. However, the present invention is not limited to this. For example, when the control system 1002 determines that the dose of the radiation exceeds a value permitted for an object, it stops the exposure to the radiation before the control unit 210 outputs a signal for stopping the exposure to the radiation. In response to this, the control unit 210 may shift to step S609 (S629 or S639). For example, when sensing a moving image as in the above-described period T1, the user stops the exposure to the radiation by instructing the control unit 210 via the control system 1002 to end the current image sensing operation and shift to the next image sensing. In response to this, the control unit 210 may shift from step S608 (S628 or S648) to step S609 (S629 or S639).

As described above, according to this embodiment, correction signals used in executing AEC in a succeeding image sensing operation are acquired between image sensing operations. The acquisition of the correction signals starts quickly in response to the end of a preceding image sensing so that the correction signals can be acquired even if the time between the image sensing operations is short. In other words, the time between the image sensing operations can be shortened while acquiring correction signals used in a succeeding image sensing operation when, for example, the image sensing operation is performed repetitively. When executing AEC, detection signals are corrected in accordance with a correction amount based on the acquired correction signals. This can suppress the influence of an afterimage arising from the emission of remaining charges generated in the detection elements 122 in the preceding image sensing. As a result, the detection accuracy of the dose of radiation entering the radiation image sensing apparatus 200 can be improved, and the quality of an obtained radiation image can be improved.

Figure 7:
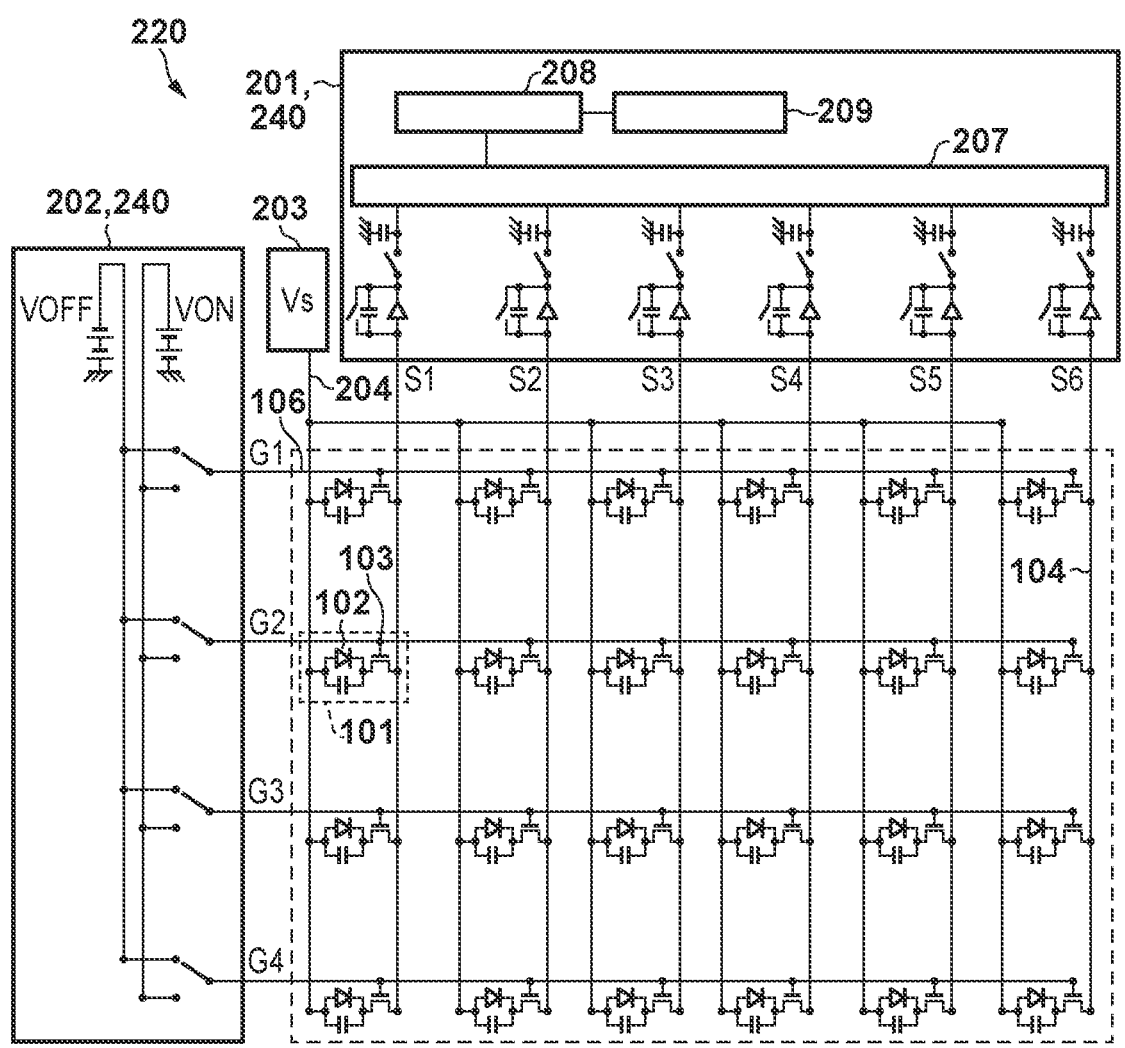
FIG. 7 is a circuit diagram showing an example of the circuit arrangement of the detection unit of the radiation image sensing apparatus in FIG. 1A.
Figure 8:
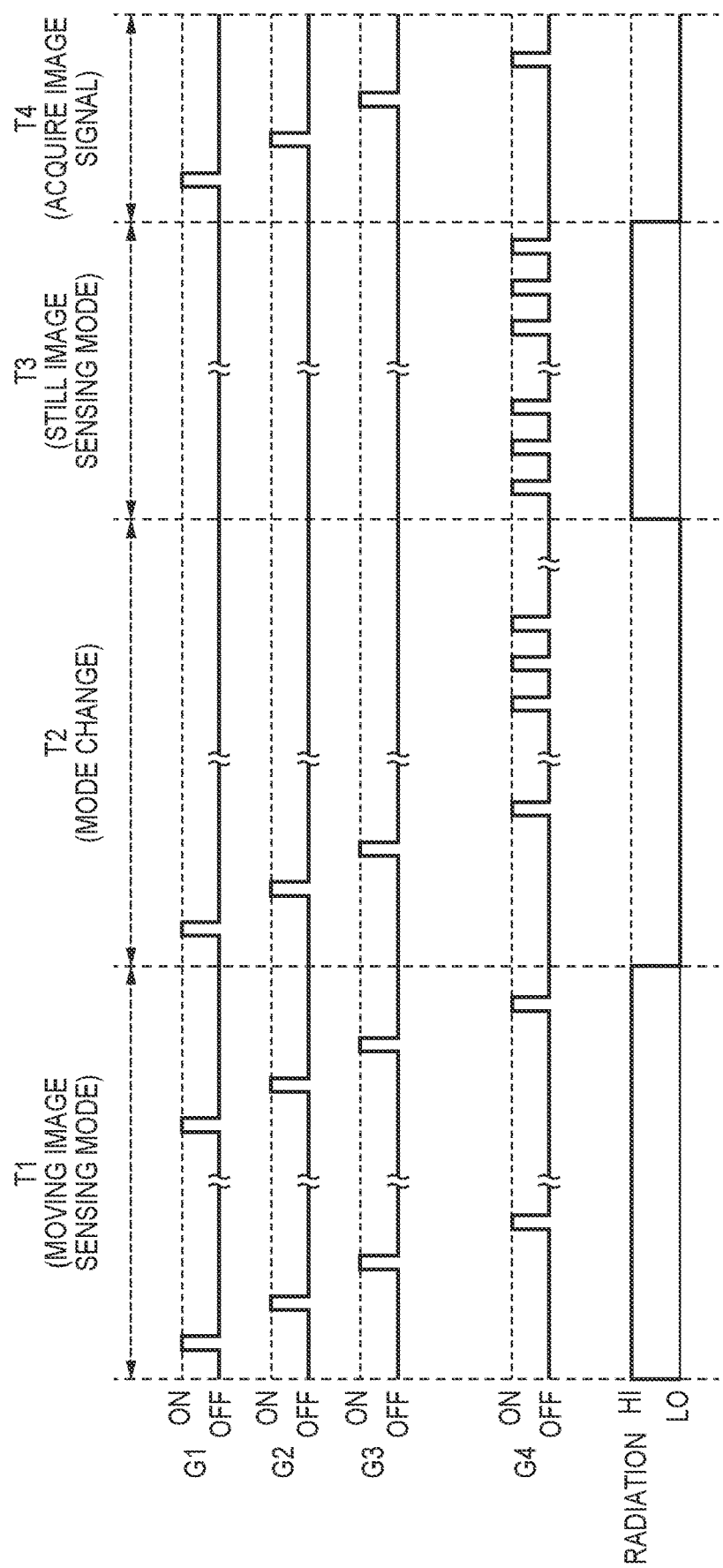
FIG. 8 is a timing chart showing the operation of the radiation image sensing apparatus in FIG. 1A.

The arrangement of a radiation image sensing apparatus according to an embodiment of the present invention will be described with reference to FIGS. 7 and 8. FIG. 7 is an equivalent circuit diagram showing the circuit arrangement of a signal detection unit 220 of a radiation image sensing apparatus 200 according to the second embodiment of the present invention. Only pixels 101 each including a conversion element 102 and a switching element 103 are arranged without arranging pixels 121 each including a conversion element 102', a detection element 122, and switching elements 103' and 123. The remaining arrangement may be the same as that in the above-described first embodiment.

Next, the operation of the radiation image sensing apparatus 200 will be described with reference to FIG. 8. In the chart shown in FIG. 8, a mode (period T1) in which a moving image is sensed is switched via a mode change (period T2) to a mode in which a still image is sensed. In the mode (periods T3 and T4) in which a still image is sensed, AEC is executed. In this embodiment, the pixels 101 are arranged in an image sensing area 230 without arranging the pixels 121 each including the detection element 122, unlike the above-described first embodiment. FIG. 8 shows a case in which AEC is executed using, as detection elements, the conversion elements 102 included in the pixels 101 in which the switching elements 103 are controlled by a gate line 106 (G4) out of the gate lines 106 (G1 to G4). More specifically, in the period T3 of FIG. 8, a control unit 210 controls a driving circuit 202 to repeat ON and OFF of the voltage of the gate line 106 (G4) and acquire detection signals for monitoring a radiation dose in real time. The control unit controls the driving circuit 202 to keep OFF the voltage of the gate lines 106 (G1 to G3), and accumulates charges in the conversion elements 102 of the pixels 101 controlled by the gate lines 106 (G1 to G3).

Even in this embodiment, in the period T2 that starts in response to the end of an image sensing operation in the period T1, the control unit 210 acquires a correction signal for correcting a detection signal in performing AEC in the period T3, similar to the above-described first embodiment. Further, in this embodiment, the control unit 210 controls to repeat ON and OFF of the voltage of the gate lines 106 (G1 to G3) while performing the operation in the period T2. Accordingly, the control unit 210 acquires a correction signal for correcting an afterimage generated by charges arising from image sensing in the period T1 and superposed in an image signal read out from each conversion element 102 in the period T4. The image signal acquired from each conversion element 102 in the period T4 is corrected by a correction amount based on the correction signal acquired from each conversion element in the period T2. This can improve the quality of an obtained radiation image. In the chart shown in FIG. 8, the correction signal of the conversion element 102 configured to acquire an image signal and the correction signal of the conversion element 102 functioning as a detection element are acquired at different timings. However, these correction signals may be acquired simultaneously. The duration of the period T2 can greatly change depending on the method, conditions, and the like used in performing the image sensing operation. Even so, the control unit 210 needs to acquire at least one correction signal from each conversion element 102 during the period T2. The method of correcting a detection signal by a correction amount based on a correction signal in the period T3 may be the same as that in the above-described first embodiment.

In this embodiment, the image sensing area 230 has a highly uniform circuit pattern in which only the pixels 101 are arranged without arranging the pixels 121, compared to the circuit pattern in the above-described first embodiment. Since neither a gate line 107 nor a detection line 105 is necessary, the design and formation of the circuit can be easy. In this embodiment, AEC is executed using the pixels 101 connected to the gate line 106 (G4). However, the pixels 101 connected to the gate lines 106 (G1 to G4) may be selected properly in accordance with an image sensing situation or an image sensing portion. Some of the conversion elements 102 arranged in the image sensing area 230 suffice to function as detection elements. The pixels 101 used in AEC are not limited to the pixels 101 connected to one gate line 106, but a plurality of gate lines 106 may be selected to use the pixels 101 connected to the gate lines 106. Signals output from the pixels 101 used in executing AEC may not be read out as image signals in the period T4. The lost image signals of the pixels 101 may be generated based on image signals output from the conversion elements 102 of the surrounding pixels 101.

In each of the above-described embodiments, the control unit 210 corrects detection signals acquired in the period T3 in accordance with a correction amount based on correction signals acquired in the period T2, detects a radiation dose in real time based on the corrected detection signals, and executes AEC using the radiation dose. However, the control unit 210 may perform exposure control of the radiation image sensing apparatus 200 using the detected radiation dose, in addition to the execution of AEC. For example, in the chart shown in FIG. 3, the control unit 210 may control the readout unit 240 (the readout circuit 201 and the driving circuit 202) to sequentially supply ON to the gate lines 106 (G1 to G4) and reset the conversion elements 102 and 102' of the pixels 101 and 121 in the period T2. Then, in the period T3, the control unit 210 may detect the start of irradiation with radiation based on a radiation dose detected in real time, stop the reset operation of the conversion elements 102 and 102' in response to the detection of the start of irradiation with radiation, and start accumulating charges. The accuracy of a radiation irradiation start automatic detection technique of detecting the start of irradiation with radiation can be improved by correcting detection signals using a correction amount based on correction signals acquired in the period T2. For example, the embodiment may be applied to a radiation irradiation end automatic detection technique of detecting the end of irradiation with radiation based on a radiation dose detected in real time in the period T3. In response to the detection of the end of irradiation with radiation, the period T3 may shift to the period T4 in which an image signal for generating a radiation image is read out from each conversion element 102.

Although the embodiments according to the present invention have been described above, the present invention is not limited to these embodiments. The above-described embodiments can be properly modified and combined without departing from the spirit and scope of the present invention.

Figure 9:
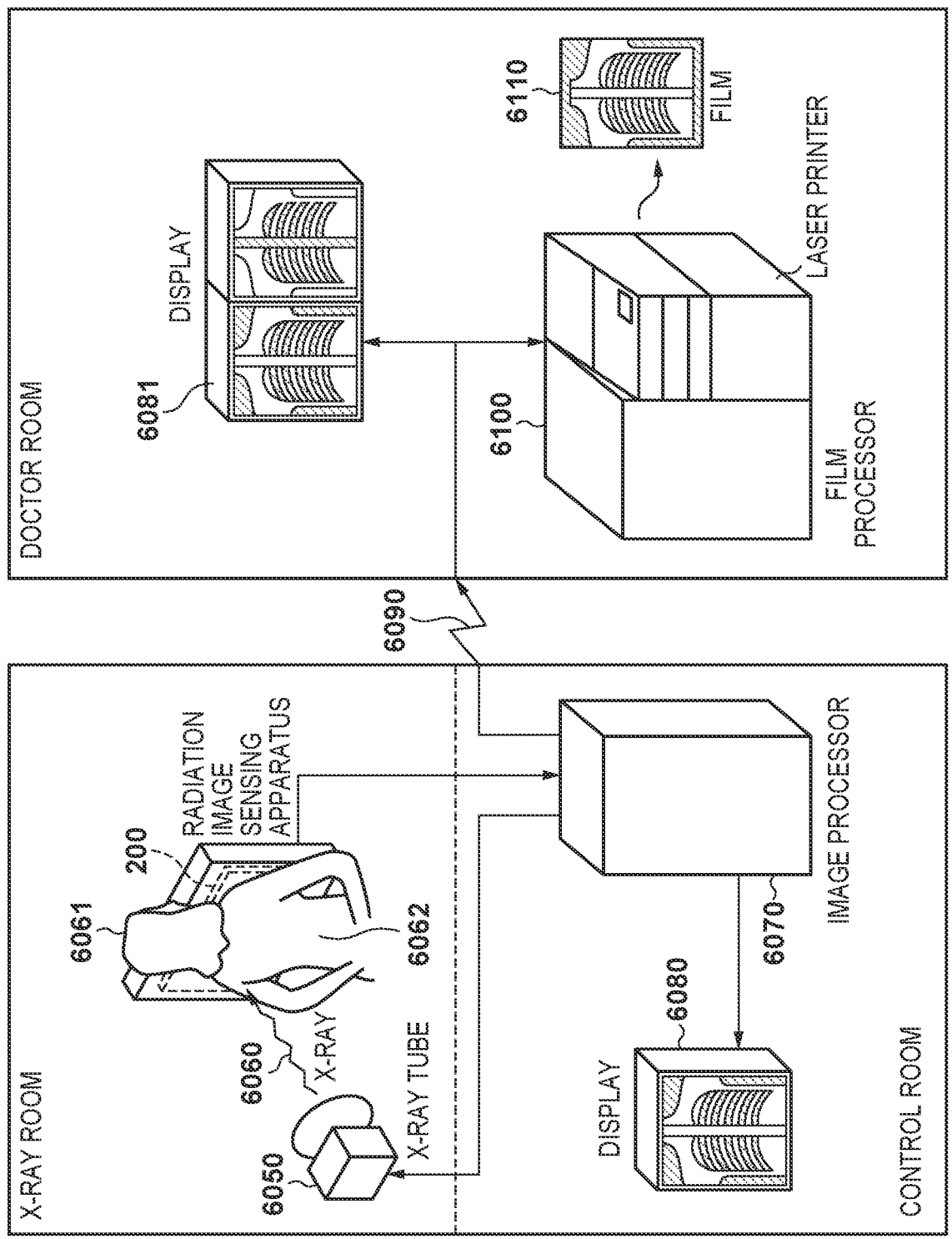
FIG. 9 is a view showing an example of the arrangement of a radiation image sensing system using the radiation image sensing apparatus in FIG. 1A.

A radiation image sensing system incorporating the radiation image sensing apparatus 200 according to the present invention will be exemplified with reference to FIG. 9. X-rays 6060 generated by an X-ray tube 6050 serving as a radiation source pass through a chest 6062 of a patient or object 6061 and enter the radiation image sensing apparatus 200 according to the present invention. The incident X-rays include information about the inside of the body of the patient or object 6061. In the radiation image sensing apparatus 200, a scintillator emits light in accordance with the incidence of the X-rays 6060, and the emitted light is photoelectrically converted by photoelectric conversion elements to obtain electrical information. This information is converted into digital data, undergoes image processing by an image processor 6070 serving as a signal processing unit, and can be observed on a display 6080 serving as a display unit in a control room.

This information can be transferred to a remote place by a transmission processing unit such as a network 6090, for example, a telephone, LAN, or Internet. This makes it possible to display the information on a display 6081 serving as a display unit in another place such as a doctor room, thus allowing a doctor in a remote place to make a diagnosis. In addition, the information can be recorded on a recording medium such as an optical disk. Furthermore, the information can also be recorded on a film 6110 serving as a recording medium by a film processor 6100.

The above solution provides a technique of improving the detection accuracy of the dose of radiation entering a radiation image sensing apparatus.

Other Embodiments

Embodiment(s) of the present invention can also be realized by a computer of a system or apparatus that reads out and executes computer executable instructions (e.g., one or more programs) recorded on a storage medium (which may also be referred to more fully as a 'non-transitory computer-readable storage medium') to perform the functions of one or more of the above-described embodiment(s) and/or that includes one or more circuits (e.g., application specific integrated circuit (ASIC)) for performing the functions of one or more of the above-described embodiment(s), and by a method performed by the computer of the system or apparatus by, for example, reading out and executing the computer executable instructions from the storage medium to perform the functions of one or more of the above-described embodiment(s) and/or controlling the one or more circuits to perform the functions of one or more of the above-described embodiment(s). The computer may comprise one or more processors (e.g., central processing unit (CPU), micro processing unit (MPU)) and may include a network of separate computers or separate processors to read out and execute the computer executable instructions. The computer executable instructions may be provided to the computer, for example, from a network or the storage medium. The storage medium may include, for example, one or more of a hard disk, a random-access memory (RAM), a read only memory (ROM), a storage of distributed computing systems, an optical disk (such as a compact disc (CD), digital versatile disc (DVD), or Blu-ray Disc (BD)™), a flash memory device, a memory card, and the like.

While the present invention has been described with reference to exemplary embodiments, it is to be understood that the invention is not limited to the disclosed exemplary embodiments. The scope of the following claims is to be accorded the broadest interpretation so as to encompass all such modifications and equivalent structures and functions.

The invention claimed is:

1. A radiation image sensing apparatus, comprising: an image sensing area configured to be used in image sensing operations of acquiring a radiation image corresponding to incidence of radiation, the image sensing area comprising a plurality of first pixels, each of the first pixels including a conversion element, and the sensing operations including a first image sensing operation and a second image sensing operation performed next to the first image sensing operation; a second pixel comprising a detection element and a switching element, configured to detect a radiation dose of radiation entering the image sensing area; a readout unit; and a control unit, wherein the control unit is configured to such that first charges in the detection element generated during incidence of radiation to the detection element in the first image sensing operation are reset by turning on the switching element after an end of the incidence of the radiation in the first image sensing operation, and the control unit is configured to correct a detection signal readout from the detection element via the switching element which is turned on by the readout unit during incidence of radiation in the second image sensing operation based on a correction amount acquired from a correction signal obtained from second charges that remain after resetting the first charges in the detection element, readout from the detection element by the readout unit, and detect a dose of incident radiation in the second image sensing operation based on the corrected detection signal.

2. The radiation image sensing apparatus according to claim 1, wherein the control unit controls the readout unit to read out a plurality of correction signals, generates a correction function corresponding to the plurality of correction signals, and determines the correction amount based on the correction function.

3. The radiation image sensing apparatus according to claim 1, wherein the control unit controls the readout unit to read out a plurality of correction signals, and determines the correction amount based on an average value of the plurality of correction signals.

4. The radiation image sensing apparatus according to claim 1, wherein the control unit controls the readout unit to read out a plurality of correction signals, and determines the correction amount using some of the plurality of acquired correction signals.

5. The radiation image sensing apparatus according to claim 1, wherein the control unit controls the readout unit to read out the correction signal and the detection signal in the same charge accumulation time.

6. The radiation image sensing apparatus according to claim 1, wherein the control unit controls the readout unit to read out a plurality of correction signals and a plurality of detection signals in the same sampling period.

7. The radiation image sensing apparatus according to claim 1, wherein as exposure control performed based on the radiation dose, the control unit detects a start of irradiation with radiation based on the radiation dose, and controls the plurality of conversion elements to accumulate charges in response to the detection of the start of irradiation with radiation.

8. The radiation image sensing apparatus according to claim 1, wherein as exposure control performed based on the radiation dose, the control unit acquires an integrated dose of incident radiation based on the radiation dose, determines in accordance with the integrated dose whether to stop exposure to the radiation, outputs in accordance with a result of the determination a signal for stopping the exposure to the radiation, and controls the readout unit to read out image signals for generating a radiation image from the respective conversion elements after irradiation with the radiation.

9. The radiation image sensing apparatus according to claim 1, wherein as exposure control performed based on the radiation dose, the control unit detects an end of irradiation with radiation based on the radiation dose and controls the readout unit to read out image signals for generating a radiation image from the respective conversion elements in response to detecting the end of irradiation with radiation.

10. The radiation image sensing apparatus according to claim 1, wherein after the end of incidence of radiation in the first image sensing operation, in the second image sensing operation the control unit corrects image signals that are read out from the respective conversion elements by the readout unit to generate a radiation image based on signals of the respective conversion elements that are read out from the plurality of conversion elements by the readout.

11. The radiation image sensing apparatus according to claim 1, wherein the detection element is arranged in the image sensing area.

12. The radiation image sensing apparatus according to claim 1, wherein one of the plurality of conversion elements functions as the detection element.

13. The radiation image sensing apparatus according to claim 1, wherein a condition for performing image sensing is different between the first image sensing operation and the second image sensing operation.

14. The radiation image sensing apparatus according to claim 1, wherein the first image sensing operation is an operation of sensing a moving image, and the second image sensing operation is an operation of sensing a still image.

15. A radiation image sensing system comprising:
the radiation image sensing apparatus according to claim 1; and
a signal processing unit configured to process a signal from the radiation image sensing apparatus.

16. A control method of a radiation image sensing apparatus comprising an image sensing area configured to be used in image sensing operations of acquiring a radiation image corresponding to incidence of radiation, the image sensing area comprising a plurality of first pixels each including a conversion element, a second pixel comprising a detection element and a switching element configured to detect radiation entering the image sensing area, and a readout unit, the method comprising the steps of:
a first step of resetting first charges in the detection element generated during incidence of radiation to the detection element in a first image sensing operation by turning on the switching element after an end of incidence of radiation in the first image sensing operation;
a second step of acquiring a correction signal obtained from second charges that remain after resetting the first charges in detection element read out from the detection element via the switching element which is turned on by the readout unit;
a third step of reading out a detection signal from the detection element by the readout unit during the incidence of the radiation in a second image sensing operation performed next to the second step; and
a fourth step of correcting the detection signal in accordance with a correction amount based on the correction signal, and detecting an incident radiation dose based on the corrected detection signal.

17. A non-transitory computer-readable storage medium storing a program for causing a computer to execute a control method of a radiation image sensing apparatus comprising an image sensing area configured to be used in image sensing operations of acquiring a radiation image corresponding to incidence of radiation, the image sensing area comprising a plurality of first pixels each including a conversion element, a second pixel comprising a detection element and a switching element configured to detect radiation entering the image sensing area, and a readout unit, the method comprising the steps of:
a first step of resetting first charges in the detection element, that are generated during incidence of radiation to the detection element in a first image sensing operation, by turning on the switching element after an end of incidence of the radiation in the first image sensing operation;
a second step of acquiring a correction signal obtained from second charges that remain after resetting the first charges in the detection element read out from the detection element via the switching element which is thereafter turned on by the readout unit;
a third step of reading out a detection signal from the detection element by the readout unit during the incidence of the radiation in a second image sensing operation performed next to the second step; and
a fourth step of correcting the detection signal in accordance with a correction amount based on the correction signal, and detecting an incident radiation dose based on the corrected detection signal.

* * * * *